United States Patent
Huang et al.

(10) Patent No.: US 10,345,254 B2
(45) Date of Patent: Jul. 9, 2019

(54) DETECTION METHOD FOR ELECTROPLATING PROCESS

(71) Applicant: Taiwan Semiconductor Manufacturing Co., Ltd., Hsinchu (TW)

(72) Inventors: Yung-Chang Huang, Taichung (TW); Jui-Mu Cho, Chupei (TW); Chien-Hsun Pan, Taichung (TW); Chun-Chih Lin, Taipei (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 28 days.

(21) Appl. No.: 15/689,195

(22) Filed: Aug. 29, 2017

(65) Prior Publication Data

US 2018/0372665 A1    Dec. 27, 2018

Related U.S. Application Data

(60) Provisional application No. 62/523,450, filed on Jun. 22, 2017.

(51) Int. Cl.
*G01N 27/26* (2006.01)
*C25D 13/18* (2006.01)
(Continued)

(52) U.S. Cl.
CPC ............ *G01N 27/26* (2013.01); *C25D 13/02* (2013.01); *C25D 13/18* (2013.01); *C25D 21/14* (2013.01); *C25D 21/18* (2013.01); *G01N 27/4166* (2013.01); *C25B 11/0473* (2013.01); *C25D 3/38* (2013.01); *H01L 22/10* (2013.01)

(58) Field of Classification Search
CPC ................ G01N 27/26–49; C25D 21/12
See application file for complete search history.

(56) References Cited

FOREIGN PATENT DOCUMENTS

TW         201443292 A       11/2014

OTHER PUBLICATIONS

Univ. of Cambridge, AC Cyclic Voltammetry (2001), https://www.ceb.cam.ac.uk/research/groups/rg-eme/teaching-notes/ac-cyclic-voltammetry (Year: 2001).*

(Continued)

*Primary Examiner* — Bryan D. Ripa
*Assistant Examiner* — Ho-Sung Chung
(74) *Attorney, Agent, or Firm* — Birch, Stewart, Kolasch & Birch, LLP

(57) ABSTRACT

Detection methods for an electroplating process are provided. A detection method includes immersing a substrate into an electrolyte solution to perform an electroplating process. The electrolyte solution includes an additive agent. The detection method also includes immersing a detection device into the electrolyte solution. The detection method further includes applying a first alternating current (AC) voltage or direct current (DC) voltage to the detection device to detect the concentration of the additive agent. In addition, the detection method includes applying a combination of a second AC voltage and a second DC voltage to the detection device to inspect the electrolyte solution. An impurity is detected in the electrolyte solution. The detection method also includes replacing the electrolyte solution containing the impurity with another electrolyte solution.

20 Claims, 10 Drawing Sheets

(51) Int. Cl.
*C25D 13/02* (2006.01)
*G01N 27/416* (2006.01)
*C25D 21/14* (2006.01)
*C25D 21/18* (2006.01)
*H01L 21/66* (2006.01)
*C25B 11/04* (2006.01)
*C25D 3/38* (2006.01)

(56) References Cited

OTHER PUBLICATIONS

Jaworski et al., Automated AC Voltammetric Sensor for Early Fault Detection and Diagnosis in Monitoring of Electroplating Processes, 25(1) Electroanalysis 278 (2013) (Year: 2013).*

Jaworski et al., Multi-way standardization of an AC voltammetric analyzer for electrometallization baths, 656 Analytica Chimica Acta 42 (2009) (Year: 2009).*

Benabida et al., Effects of linseed oil additive on the electroplating of tin on mild steel, 6(6) Der Pharma Chemica 285 (2014) (Year: 2014).*

Armstrong, Equivalent Circuits for Electrochemical Cells, J. Electroanal. Chem. 40 (1972) (Year: 1972).*

* cited by examiner

DETECTION METHOD FOR ELECTROPLATING PROCESS

CROSS REFERENCE TO RELATED APPLICATIONS

This Application claims the benefit of U.S. Provisional Application No. 62/523,450, filed on Jun. 22, 2017, the entirety of which is incorporated by reference herein.

BACKGROUND

Semiconductor devices are used in a variety of electronic applications, such as personal computers, cell phones, digital cameras, and other electronic equipment. The semiconductor industry continues to improve the integration density of various electronic components (e.g., transistors, diodes, resistors, capacitors, etc.) by continual reductions in minimum feature size, which allows more components to be integrated into a given area. These smaller electronic components also require smaller packages that utilize less area than the packages of the past, in some applications.

During the manufacturing of the semiconductor devices, various processing steps are used to fabricate integrated circuits on a semiconductor wafer. For example, the processes include an electroplating process for deposition of conductive layers over the semiconductor wafer, thereby forming the integrated circuits. Generally, an electroplating process includes depositing or plating out positively charged ions (such as metal ions) onto a negatively charged substrate (such as the semiconductor wafer), which is used as a source of electrons. As a result, a seed layer (or a metal layer) is first deposited over the semiconductor wafer to provide an electrical path across the surfaces. An electrical current is then supplied to the seed layer, thereby electroplating the semiconductor wafer surface with an appropriate metal (such as copper, aluminum or another suitable material).

An electroplating device or system is used to perform the electroplating process. For example, the electroplating device includes an electrolyte tank, a container or in the electrolyte tank and an anode in the container. The negatively charged substrate to be electroplated is in contact with a plating solution in the container so as to deposit a conductive layer thereon. However, variations in the plating solution may reduce the quality of the electroplating. Therefore, the plating solution needs to be kept clean and have a chemical composition within specific limits.

Although numerous improvements to the electroplating process have been invented, they have not been entirely satisfactory in all respects. Consequently, it would be desirable to provide solutions to improve the quality of the electroplating process, thereby enhancing the electrical performance and reliability of the semiconductor devices.

BRIEF DESCRIPTION OF THE DRAWINGS

Aspects of the present disclosure are best understood from the following detailed description when read with the accompanying figures. It should be noted that, in accordance with the standard practice in the industry, various features are not drawn to scale. In fact, the dimensions of the various features may be arbitrarily increased or reduced for clarity of discussion.

DETAILED DESCRIPTION

Figure 1A:
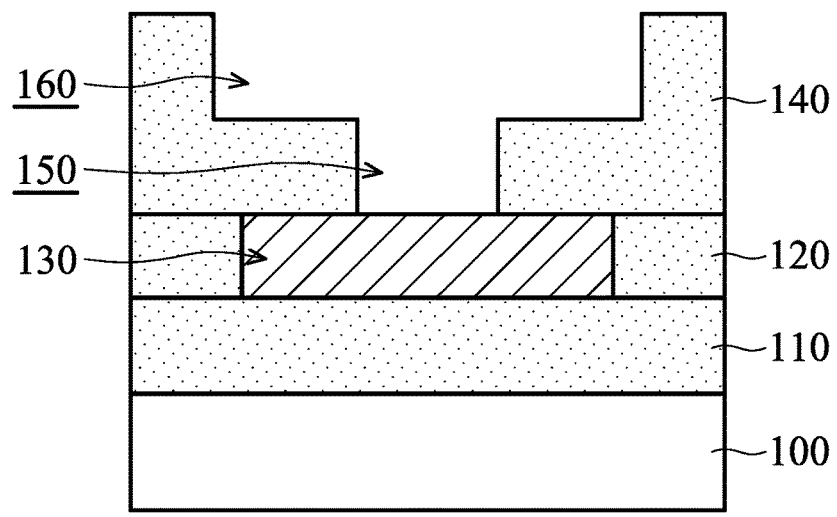
FIGS. 1A-1C are cross-sectional views of various stages of a process for forming a semiconductor device structure, in accordance with some embodiments.

The following disclosure provides many different embodiments, or examples, for implementing different features of the subject matter provided. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Some embodiments of the disclosure are described. Additional operations can be provided before, during, and/or after the stages described in these embodiments. Some of the stages that are described can be replaced or eliminated for different embodiments. Some of the features described below can be replaced or eliminated and additional features can be added for different embodiments. Although some embodiments are discussed with operations performed in a particular order, these operations may be performed in another logical order.

Figure 1B:
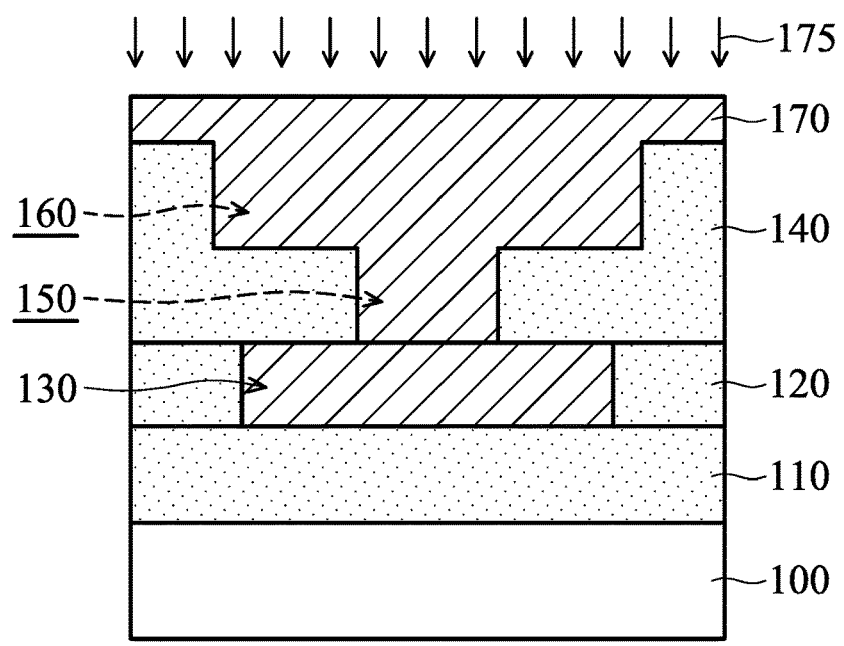
Figure 1C:
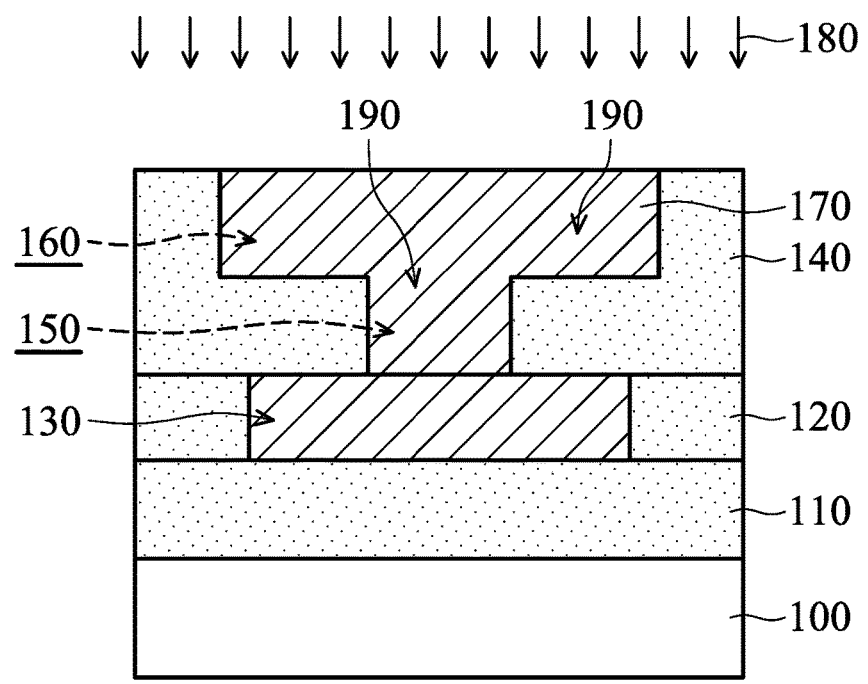

FIGS. 1A-1C are cross-sectional views of various stages of a process for forming a semiconductor device structure, in accordance with some embodiments. As shown in FIG. 1A, a semiconductor substrate 100 is provided. The semiconductor substrate 100 may include silicon, germanium, a compound semiconductor (such as silicon germanium, gallium arsenide, or silicon carbide), or another suitable semiconductor material. In some embodiments, the semiconductor substrate 100 includes a semiconductor-on-insulator (SOI) substrate.

In some embodiments, various device elements are formed in and/or over the semiconductor substrate 100. The device elements are not shown in figures for the purpose of simplicity and clarity. Examples of the various device elements include transistors, diodes, another suitable element, and a combination thereof.

In some embodiments, an interconnection structure (which will be described in more detail later) is formed over the semiconductor substrate 100. Various device elements are interconnected through the interconnection structure over the semiconductor substrate 100 to form integrated circuit devices. The interconnection structure includes multiple dielectric layers containing an interlayer dielectric (ILD) layer and one or more inter-metal dielectric (IMD) layers. The interconnection structure also includes multiple conductive features formed in the ILD and IMD layers. The conductive features may include conductive lines, conductive vias, and/or conductive contacts.

More specifically, as shown in FIG. 1A, a dielectric layer 110 is deposited over the semiconductor substrate 100. The dielectric layer 110 may serve as an ILD or IMD layer. The dielectric layer 110 covers device elements formed in and/or over the semiconductor substrate 100. In some embodiments, the dielectric layer 110 is made of or includes a low dielectric constant (low-k) material, silicon oxide, silicon oxynitride, one or more other suitable materials, or a combination thereof. Multiple conductive features (not shown) are formed in the dielectric layer 110 and electrically connected to the device elements.

As shown in FIG. 1A, a dielectric layer 120 is deposited over the dielectric layer 110. The dielectric layer 120 may serve as an IMD layer. Multiple conductive features are formed in the dielectric layer 120. A conductive feature 130 is shown in FIG. 1A as an example. The conductive feature 130 may be a conductive line or another suitable conductive feature. The conductive feature 130 may be a single or dual damascene structure. The conductive feature 130 is electrically connected to the device elements through the conductive features in the dielectric layer 110.

As shown in FIG. 1A, a dielectric layer 140 is deposited over the dielectric layer 120. The dielectric layer 140 serves as an IMD layer of an interconnection structure. The dielectric layer 140 covers the conductive features 130.

Afterwards, one or more etching processes (such as a dry etching process and/or a wet etching process) are performed over the dielectric layer 140. As a result, multiple via holes and trenches are formed. A via hole 150 and a trench 160 in the dielectric layer 140 are shown in FIG. 1A as an example.

As shown in FIG. 1B, a conductive layer 170 is deposited over the dielectric layer 140 and fills the via hole 150 and the trench 160, in accordance with some embodiments. In some embodiments, an electroplating process 175 is performed over the dielectric layer 140 to deposit the conductive layer 170. The electroplating process 175 will be described in more detail later. In some embodiments, the conductive layer 170 is made of or includes copper (Cu), aluminum (Al), tungsten (W), titanium (Ti), cobalt (Co), nickel (Ni), gold (Au), platinum (Pt), one or more other suitable materials, or a combination thereof.

Although FIG. 1B shows that the conductive layer 170 is a single layer, embodiments of the disclosure are not limited thereto. The conductive layer 170 may be a multi-layer structure including conductive sub-layers. For example, the conductive sub-layers include a metal-filling layer, a seed layer, a diffusion barrier layer, one or more other suitable layers, or a combination thereof. The conductive sub-layers are not shown in figures for the purpose of simplicity and clarity.

In some embodiments, a planarization process 180 (such as chemical mechanical polishing process or another applicable process) is performed over the conductive layer 170. The conductive layer 170 is thinned until the dielectric layer 140 is exposed. As a result, the remaining portions of the conductive layer 170 in the via hole 150 and the trench 160 form multiple conductive features 190 in the dielectric layer 140, as shown in FIG. 1C. The conductive features 190 in the via hole 150 and the trench 160 may be a conductive via and a conductive line, respectively.

Subsequently, one or more dielectric layers and multiple conductive features are formed over the dielectric layer 140 and the conductive features 190 to continue the formation of the interconnection structure. For example, in some embodiments, the operations illustrated in FIGS. 1A-1C are repeated one or more times to continue the formation of the interconnection structure.

In accordance with some embodiments, the electroplating process 175 (or electrochemical plating (ECP) process) includes immersing the structure shown in FIG. 1A in an electrolyte solution. The electrolyte solution includes electrolyte for deposition of the conductive layer 170. In some embodiments, the electrolyte solution further includes one or more additive agents, which may aid in controlling plating characteristics. Examples of the additive agents include accelerators, suppressors, levelers, one or more other suitable additive agents, and a combination thereof. However, embodiments of the disclosure are not limited.

The accelerators and suppressors are used to control the plating rate of the electroplating process 175. For example, the accelerators may increase the depositing rate at the bottom of the via hole 150 or the trench 160 during the electroplating process 175. On the other hand, the suppressors may slow down the depositing at the sidewalls of the via hole 150 or the trench 160 during the electroplating process 175. It can be ensured that a void or vacancy is not formed in the conductive layer 170 inside the via hole 150 and the trench 160 (i.e., the conductive features 190 are substantially void-free). As a result, resistance capacitance (RC) delay time is prevented from being increased. The circuit performance is increased.

The levelers are used to provide a leveling effect by giving the conductive layer 170 a smooth surface. For example, the conductive layer 170 may be prevented from being thicker at the via hole 150 or the trench 160 while being thinner around he via hole 150 or the trench 160. As a result, the uniformity of the conductive layer 170 is improved.

Changes and/or chemical pollutions in the electrolyte solution may reduce the quality and effectiveness of the electroplating. For example, in some cases, one or more contaminants may be mixed into the electrolyte solution before, during and/or after the electroplating process 175. Contaminants in the electrolyte solution may include one or more kinds of oil and/or cleaning agent. The oil and/or cleaning agent may be leaked or sprayed from any part of an electroplating device or system. As a result, the additive agents (such as the accelerators) may lose their functions due to the cleaning agent (such as $H_2O_2$). Alternatively, the bonding or adhesion between the conductive layer 170 and the dielectric layer 140 may be reduced due to the oil. As a result, the conductive layer 170 may be pulled and then peeled off during the planarization process 180.

In some cases, the additive agents may decompose during the electroplating process 175. As a result, one or more by-products may be formed in the electrolyte solution. The decomposed additive agents may lose their functions. The quality of the electroplating may be negatively affected, for example a void may be formed in the conductive layer 170 inside the via hole 150 and the trench 160.

In accordance with some embodiments, an electrolyte detecting and analysis method is used to detect and monitor the chemical composition and concentration of the electrolyte solution in real time by an electrolyte analysis system. The electrolyte analysis system uses voltammetry measurement technology. The voltammetry measurement technology uses electrodes (such as metal probes) immersed in the electrolyte solution to measure the concentration of electrolyte in the inorganic component and organic additives by alternating current (AC) and/or direct current (DC) voltammetry analysis. Accordingly, it can be ensured that the electrolyte solution has a chemical composition within specific concentrations.

FIGS. 2A-2D are cross-sectional views of various stages of an electroplating process, in accordance with some embodiments. An ECP device 200 (or a plating device) is shown in FIGS. 2A-2D as an example and not a limitation to the disclosure. Embodiments of the disclosure can be applied to other suitable ECP apparatuses.

Figure 2A:
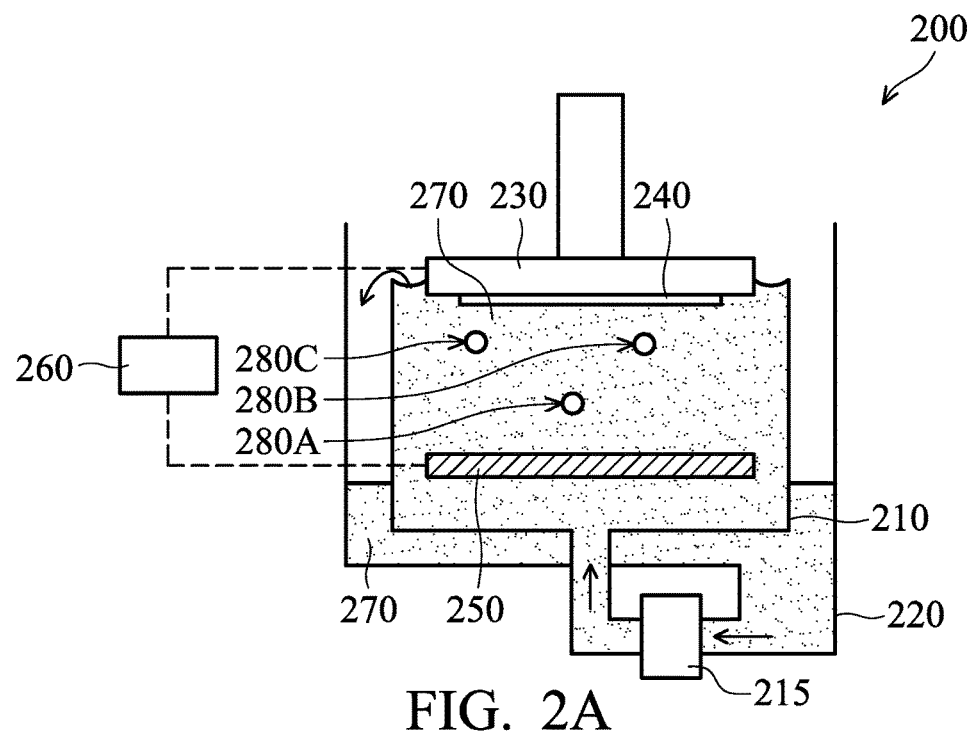
FIGS. 2A-2D are cross-sectional views of various stages of an electroplating process, in accordance with some embodiments.

As shown in FIG. 2A, the ECP device 200 includes a plating bath 210, a pump 215, a reservoir 220, a holder assembly 230, an anode 250, and a power supply 260, in accordance with some embodiments. The ECP device 200 may include one or more additional elements, which are not shown in figures for the purpose of simplicity and clarity.

An electrolyte solution 270 (or a plating solution) is prepared and provided in the plating bath 210. The electrolyte solution 270 includes electrolyte for deposition of a conductive layer. For example, the electrolyte solution 270 may include $CuSO_4$, HCl and $H_2O$. However, embodiments of the disclosure are not limited thereto. The electrolyte solution 270 may include other suitable materials. In some embodiments, the electrolyte solution 270 further includes one or more additive agents. An accelerator 280A, a suppressor 280B and a leveler 280C are shown in FIG. 2A as an example and not a limitation to the disclosure.

In some embodiments, the accelerator 280A is made of or includes bis(sodiumsulfopropyl)disulfide (SPS), 3-mercapto-1-propanesulfonic acid (MPS), 1-propane sulfonic acid, 3-(ethoxy-thioxomethyl)-thiol sodium salt (OPX), one or more other suitable materials, or a combination thereof. In some embodiments, the suppressor 280B is made of or includes polyethylene oxide (PEO), polypropylene oxide (PPO), polyethylene glycol (PEG), polypropylene glycol (PPG), one or more other suitable materials, or a combination thereof. In some embodiments, the leveler 280C is made of or includes thiourea, benzotriazole (BTA), poly(vinyl pyrrolidone) (PVP), one or more other suitable materials, or a combination thereof.

The electrolyte solution 270 is continually supplied to the plating bath 210 by the pump 215. The electrolyte solution 270 may overflow from the plating bath 210 to the reservoir 220. Afterwards, the electrolyte solution 270 in the reservoir 220 is returned to the plating bath 210 by the pump 215. The electrolyte solution 270 in the reservoir 220 may or may not be filtered before being returned to the plating bath 210.

As shown in FIG. 2A, the power supply 260 (such as a DC power supply) is electrically coupled to the anode 250 in the plating bath 210 and the holder assembly 230. A substrate 240 (such as the structure shown in FIG. 1A) is mounted to the holder assembly 230. The substrate 240 is then placed in the plating bath 210 to be immersed in the electrolyte solution 270. The power supply 260 provides a negative output to the substrate 240 and a positive output to the anode 250 so as to perform an electroplating process (such as the electroplating process 175 shown in FIG. 1B).

During the electroplating process, the electrolyte solution 270 flows upwards to the center of the substrate 240 and then radially outward and across the substrate 240. An electrochemical reaction (e.g., $Cu^{2+}+2e^-\rightarrow Cu$) on the substrate 240 results in deposition of the electrically conductive layer (e.g., Cu) thereon. Embodiments of the disclosure can be applied to other suitable electrochemical reaction and the deposition of other conductive materials.

Figure 2B:
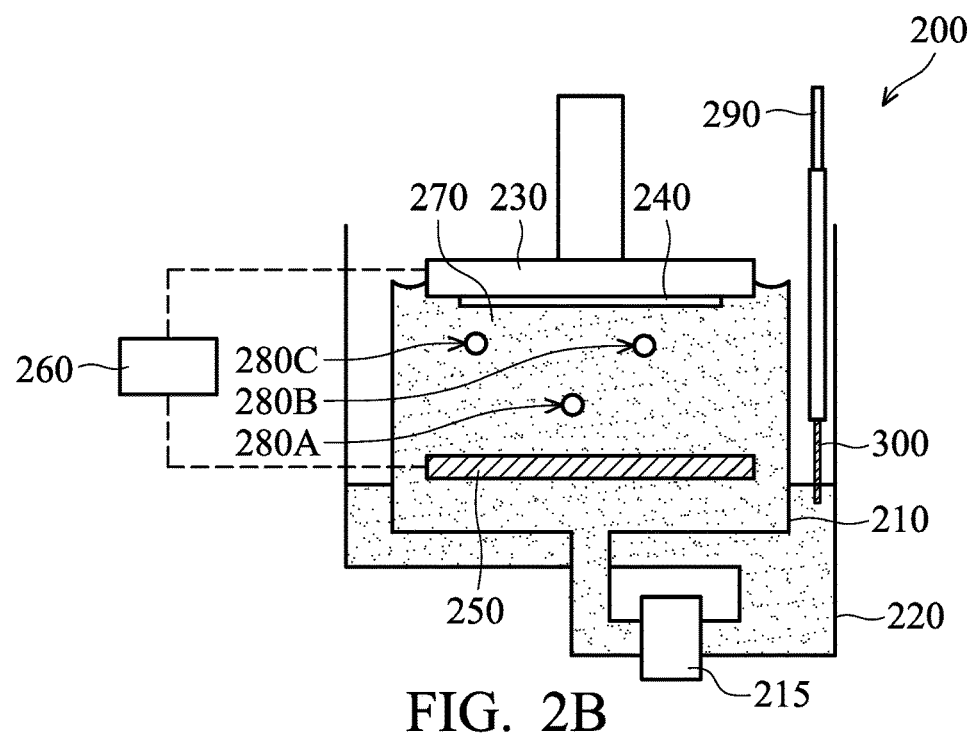

As shown in FIG. 2B, a detection device 290 (or an electrolyte analysis system) is partially placed in the electrolyte solution 270, in accordance with some embodiments. The detection device 290 is used to detect and monitor the chemical composition and concentration of the electrolyte solution 270. The detection device 290 may be a real-time analyzer (RTA).

More specifically, the detection device 290 may be used to detect and monitor the concentrations of the accelerator 280A, the suppressor 280B and/or the leveler 280C. When the concentrations of the accelerator 280A, the suppressor 280B and/or the leveler 280C are reduced, more additive agents are added in the electrolyte solution 270. The concentration of the electrolyte solution 270 may be fine-tuned according to detected results by the detection device 290. Accordingly, it can be ensured that the chemical composition of the electrolyte solution 270 maintains within specific concentrations to well-control plating characteristics.

For example, a power supply (not shown) is coupled to the detection device 290. AC or DC is input to the detection device 290 so as to detect the concentration of an additive agent (i.e., one of the accelerator 280A, the suppressor 280B and the leveler 280C). Since the detection device 290 may detect one of the accelerator 280A, the suppressor 280B and the leveler 280C at one time, only AC or DC is input to the detection device 290. Different alternating or direct currents may be used to detect the accelerator 280A, the suppressor 280B and the leveler 280C.

In some embodiments, the AC current, which is applied to the detection device 290 for detecting an additive agent, is in a range from about 100 mA to about 5 A. In some embodiments, the AC frequency, which is applied to the detection device 290 for detecting an additive agent, is in a range from about 10 Hz to about 4000 Hz. In some embodiments, the DC voltage, which is applied to the detection device 290 for detecting an additive agent, is in a range from about −10 V to about +10 V. It should be noted that these ranges are only examples and are not a limitation to the disclosure.

The detection device 290 includes one or more metal probes for detection. The metal probes may be made of or include Pt, one or more other suitable materials, or a combination thereof. One probe 300 is shown in FIG. 2B as an example and not a limitation to the disclosure. Although FIG. 2B shows that the probe 300 is dipped in the electrolyte solution 270 in the reservoir 220 during the electroplating process, embodiments of the disclosure are not limited thereto. In some other embodiments, the probe 300 is immersed in the electrolyte solution 270 before and/or after the electroplating process. The probe 300 may be immersed in the electrolyte solution 270 in the plating bath 210 before, during and/or after the electroplating process.

Figure 2C:
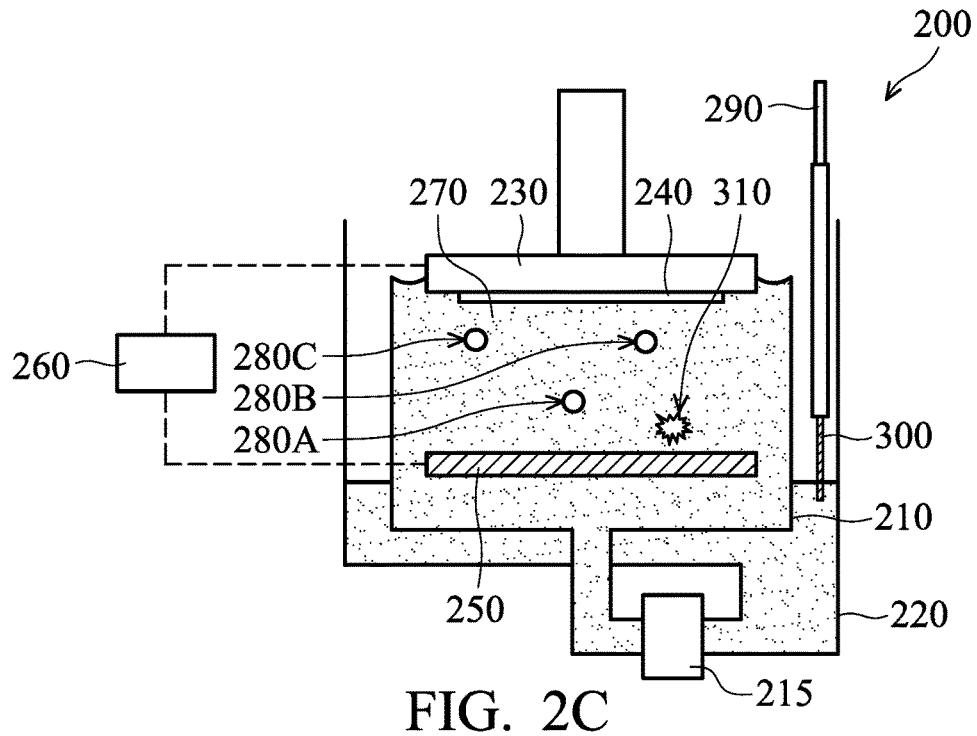

In accordance with some embodiments, the probe 300 of the detection device 290 is also used to detect and monitor the concentration of one or more impurities. More specifically, the probe 300 is immersed in the electrolyte solution 270 to examine contamination and/or monitor the concentration of by-products. In some embodiments, the electrolyte solution 270 is in direct contact with the probe 300 and with the substrate 240 at the same time during the electroplating process, as shown in FIG. 2C. In some other embodiments, the electrolyte solution 270 is in direct contact with one of the probe 300 and the substrate 240 but separated from another of the probe 300 and the substrate 240.

As shown in FIG. 2C, there is an impurity 310 in the electrolyte solution 270, in accordance with some embodiments. It should be noted that the impurity 310 shown in FIG. 2C is only an example and not a limitation to the disclosure. The impurity 310 may include one or more contaminants and/or one or more by-products.

Contaminants in the electrolyte solution 270 may include one or more kinds of oil and/or cleaning agent. The cleaning agent (or cleaning solution) may be used to wash the substrate 240. The cleaning agent may be made of or include $H_2O_2$, one or more other materials, or a combination thereof. The oil and/or cleaning agent may be leaked or sprayed from any part or element of the ECP device 200 (or an ECP system including the ECP device 200) into the plating bath 210 or the reservoir 220 before, during and/or after the electroplating process. The by-products may be formed in the electrolyte solution 270 since the accelerator 280A, the suppressor 280B and/or the leveler 280C may decompose during the electroplating process.

The power supply (not shown) provides both AC and DC (such as the 2nd harmonic AC and DC current) to the detection device 290 so as to examine the impurity 310 in the electrolyte solution 270. An oxidation reaction may be induced in the electrolyte solution 270. As a result, the species and the concentration of the impurity 310 can be identified according to feedback or responses from the electrolyte solution 270 to the detection device 290. Contaminants and by-products in the electrolyte solution 270 may be detected and identified in the same stage or different stages.

In some embodiments, AC and DC are simultaneously input to the detection device 290 to inspect the impurity 310 while only AC or DC is input to the detection device 290 to inspect an additive agent. The method of detecting the impurity 310 will be described in more detail later.

In some embodiments, the AC current, which is applied to the detection device 290 for examining the impurity 310, is in a range from about 1E-6 A to about 5 A. The AC current for detecting the impurity 310 may be less than, substantially equal to, or greater than the AC current for detecting an additive agent.

In some embodiments, the AC frequency, which is applied to the detection device 290 for examining the impurity 310, is in a range from about 5 Hz to about 3E+6 Hz. The AC frequency for detecting the impurity 310 may be less than, substantially equal to, or greater than the AC frequency for detecting an additive agent.

In some embodiments, the DC voltage, which is applied to the detection device 290 for examining the impurity 310, is in a range from about −5 V to about 10 V. The DC voltage for detecting the impurity 310 may be less than, substantially equal to, or greater than the DC voltage for detecting an additive agent. It should be noted that these ranges about AC and DC are only examples and are not a limitation to the disclosure.

In some embodiments, the electrolyte solution 270 is examined by the probe 300 for about 10 to about 40 minutes. In other words, the probe 300 may be dipped in the electrolyte solution 270 for about 10 to about 40 minutes so as to detect one or more of additive agents, contaminants and by-products. The probe 300 may be dipped in the electrolyte solution 270 for about 4 to about 10 minutes so as to detect contaminants and/or by-products. In some embodiments, the time for detecting contaminants and/or by-products is different from (such as shorter than) the time for detecting additive agents, but embodiments of the disclosure are not limited. It should be noted that these ranges are only examples and are not a limitation to the disclosure.

In some embodiments, the electrolyte solution 270 is inspected by the probe 300 of the detection device 290 per about 20 to about 300 minutes. The probe 300 may detect additive agents, contaminants and by-products per about 20 to about 300 minutes. For example, in some embodiments, the probe 300 is immersed into the electrolyte solution 270 to detect each of additive agents, contaminants and by-products in the electrolyte solution 270. Afterwards, the probe 300 is removed from the electrolyte solution 270 (as shown in FIG. 2A). After about 20 to about 300 minutes, the probe 300 is immersed into the electrolyte solution 270 again to detect each of additive agents, contaminants and by-products (as shown in FIG. 2B or 2C). These steps may be repeated one or more times during and between multiple electroplating processes.

The detection sequence of additive agents, contaminants and by-products is not limited. The probe 300 may first inspect additive agents and then inspect contaminants and by-products. Accordingly, both AC and DC are first applied to the detection device 290 and then only AC or DC is applied to the detection device 290. Alternatively, the probe 300 may first inspect contaminants and/or by-products and then inspect additive agents. Accordingly, only AC or DC is first applied to the detection device 290 and then both AC and DC are applied to the detection device 290.

Figure 2D:
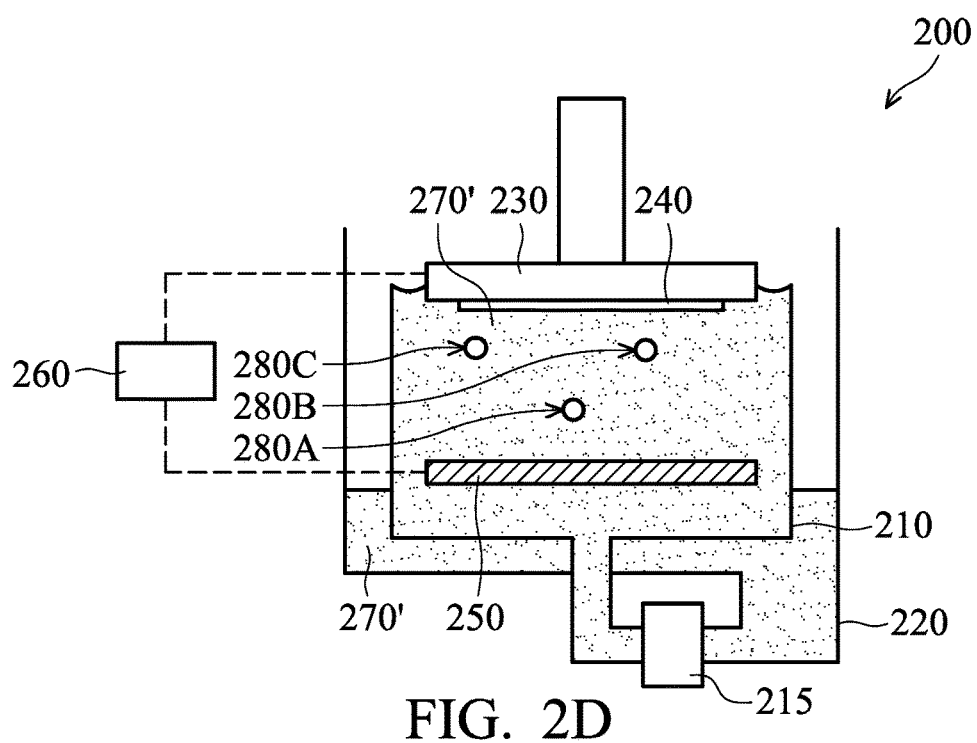

In some embodiments, multiple substrates (such as the substrate 240) are sequentially held by the holder assembly 230 and transferred into the ECP device 200. The ECP device 200 performs an electroplating process over each of the substrates. For example, the substrate 240 shown in FIG. 2A is removed from the ECP device 200 and another substrate 240 is transferred into the ECP device 200, as shown in FIG. 2C or 2D. The probe 300 may be immersed in the electrolyte solution 270 during and/or between electroplating processes of multiple substrates.

When the impurity 310 is detected in electrolyte solution 270 and/or the concentration of the impurity 310 is greater than a predetermined concentration, the electrolyte solution 270 is replaced with a new electrolyte solution 270', as shown in FIGS. 2C and 2D. The electrolyte solution 270 is replaced with the electrolyte solution 270' after the removal of the detection device 290 from the electrolyte solution 270. The electrolyte solution 270' and the original electrolyte solution 270 shown in FIG. 2A have substantially the same composition, as illustrated in the aforementioned embodiments, and therefore are not repeated. The electrolyte solution 270' is cleaner than the electrolyte solution 270 shown in FIG. 2C. The electrolyte solution 270' is substantially free of the impurity 310.

In some embodiments, the probe 300 is immersed in the electrolyte solution 270 one or more times. The electrolyte solution 270 may be replaced with the electrolyte solution 270' after one or more rounds of detection by the probe 300. Similarly, in some embodiments, the probe 300 is immersed in the electrolyte solution 270' (similar to the view shown in FIG. 2B) one or more times. The electrolyte solution 270' may be subsequently replaced with another new electrolyte solution after one or more rounds of detection by the probe 300. As a result, the ECP device 200 can perform electroplating processes with better quality over multiple substrates. Therefore, the electrical performance and reliability of the conductive layer 170, which are deposited using the ECP device 200, is enhanced significantly.

Figure 3:
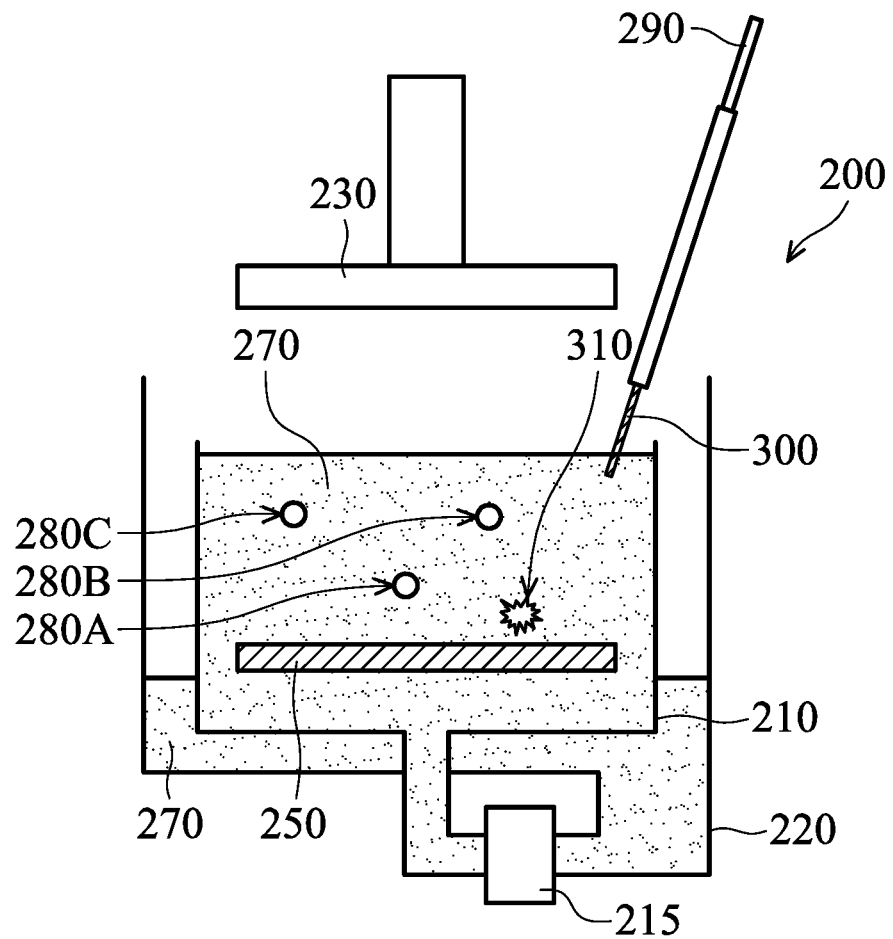
FIG. 3 is a cross-sectional view of one of various stages of an electroplating process, in accordance with some embodiments.

Many variations and/or modifications can be made to embodiments of the disclosure. For example, the detection position of the probe 300 is not limited. FIG. 3 is a cross-sectional view of one of various stages of an electroplating process, in accordance with some embodiments. The ECP device 200 shown in FIG. 3 is substantially the same or similar to those shown in FIGS. 2A-2D. In some embodiments, the materials, methods, and/or benefits illustrated in the aforementioned embodiments can also be applied in the embodiments illustrated in FIG. 3, and are therefore not repeated.

As shown in FIG. 3, the probe 300 of the detection device 290 is inserted into the electrolyte solution 270 in the plating bath 210, in accordance with some embodiments. The examination or detection of the probe 300 is performed after and/or before an electroplating process. As a result, there is no substrate 240 in the ECP device 200, as shown in FIG. 3. Alternatively, the substrate 240 may be held by the holder assembly 230 but not placed in the plating bath 210.

However, embodiments of the disclosure are not limited. In some other embodiments, the probe 300 is dipped in the electrolyte solution 270 in the plating bath 210 during an electroplating process over the substrate 240. The detection of the probe 300 in the plating bath 210 does not interrupt the electroplating process in the plating bath 210.

Figure 4:
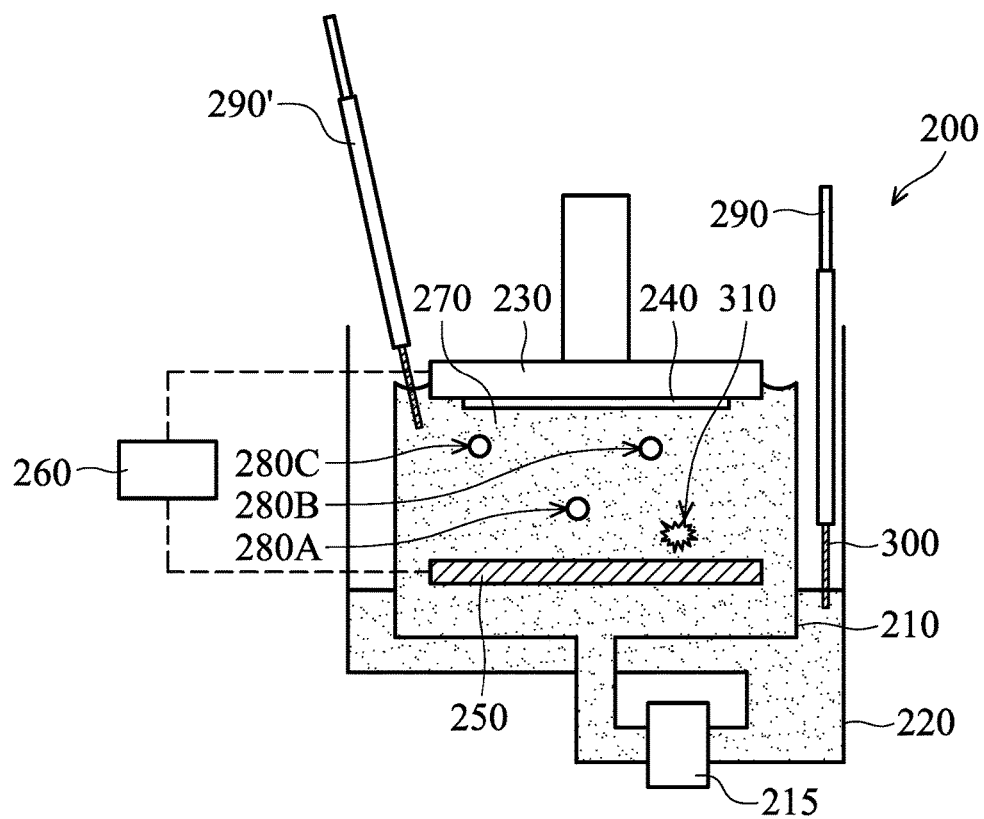
FIG. 4 is a cross-sectional view of one of various stages of an electroplating process, in accordance with some embodiments.

Many variations and/or modifications can be made to embodiments of the disclosure. For example, various probes may be used to examine the electrolyte solution 270. FIG. 4 is a cross-sectional view of one of various stages of an electroplating process, in accordance with some embodiments. The ECP device 200 shown in FIG. 4 is substantially the same or similar to those shown in FIGS. 2A-2D. In some embodiments, the materials, methods, and/or benefits illustrated in the aforementioned embodiments can also be applied in the embodiments illustrated in FIG. 4, and are therefore not repeated.

As shown in FIG. 4, there are multiple detection devices 290 and 290' in the ECP device 200, in accordance with some embodiments. The detection device 290' is substantially the same or similar to the detection device 290, and therefore are not repeated. The detection device 290' is inserted into the plating bath 210 while the detection device 290 is inserted into the reservoir 220.

In some embodiments, the detection devices 290 and 290' are separately used to detect additive agents (e.g., the accelerator 280A, the suppressor 280B and/or the leveler 280C) and the impurity 310 (e.g., contaminants and by-products). The detection device 290 may be immersed in the electrolyte solution 270 for a longer time than the detection device 290'. In other words, the detection device 290' may be removed from the electrolyte solution 270 before the removal of the detection device 290 from the electrolyte solution 270. Many variations and/or modifications can be made to embodiments of the disclosure. In some other embodiments, the detection devices 290 and 290' are separately used to detect contaminants and by-products.

In some embodiments, the detection devices 290 and 290' are used together in the same stage (such as in the same electroplating process). Accordingly, AC and DC may be simultaneously input to the detection device 290 to inspect the impurity 310, and AC or DC is input to the detection device 290' to inspect an additive agent during the same electroplating process. However, embodiments of the disclosure are not limited. In some other embodiments, the detection devices 290 and 290' are used separately in different stages (such as different electroplating processes).

Figure 5A:
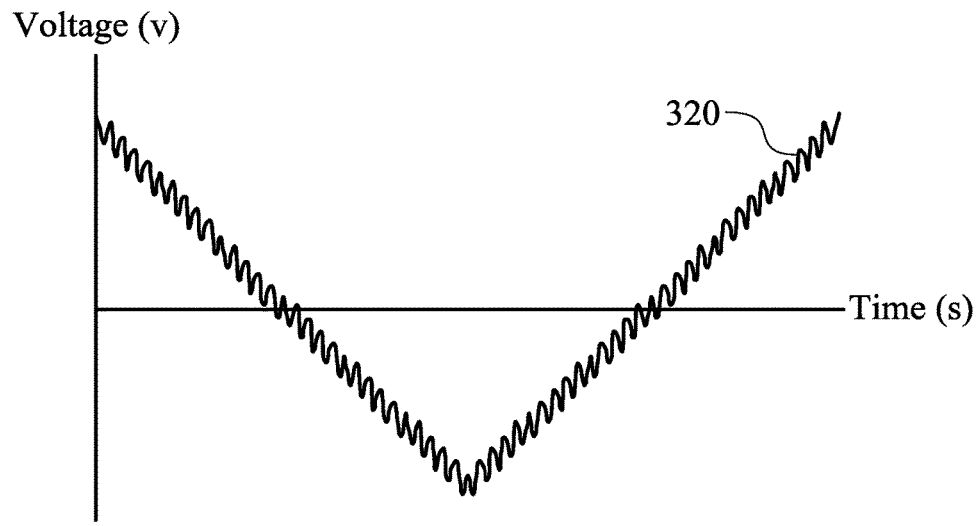
FIG. 5A is a diagram showing the input voltage of a detection device, in accordance with some embodiments.

As mentioned above, AC and DC are supplied together to the detection device 290 (and/or the detection device 290') so as to examine the impurity 310 in the electrolyte solution 270 (or the electrolyte solution 270'). As shown in FIG. 5A, the input voltage 320, which is applied to the detection device 290, periodically reverses direction. Since the period is greatly small, the input voltage 320 has a main waveform, which is V-shaped or inversed V-shaped. The input voltage 320 is shown in FIG. 5A as an example and not a limitation to the disclosure.

Figure 5B:
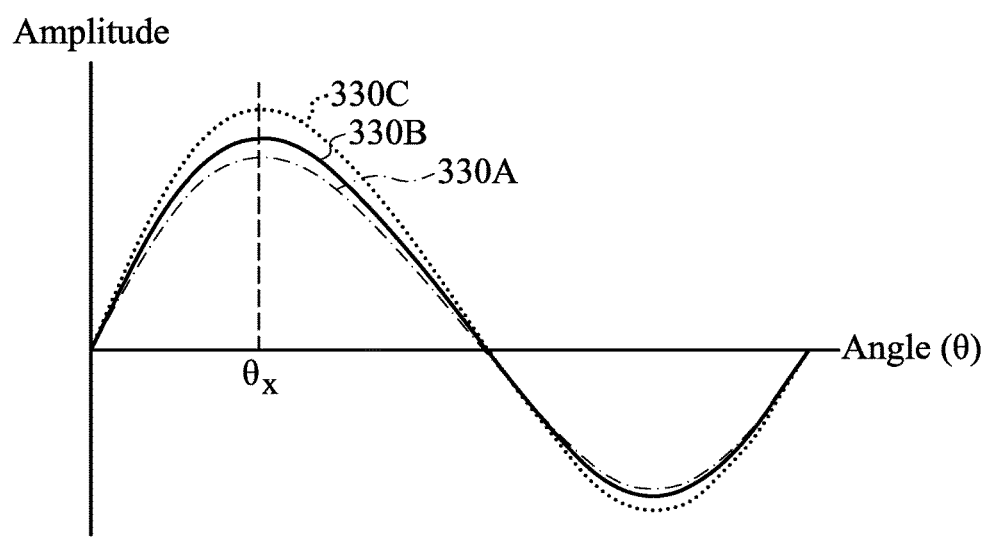
FIG. 5B is a diagram showing the output signal of a detection device, in accordance with some embodiments.
Figure 5C:
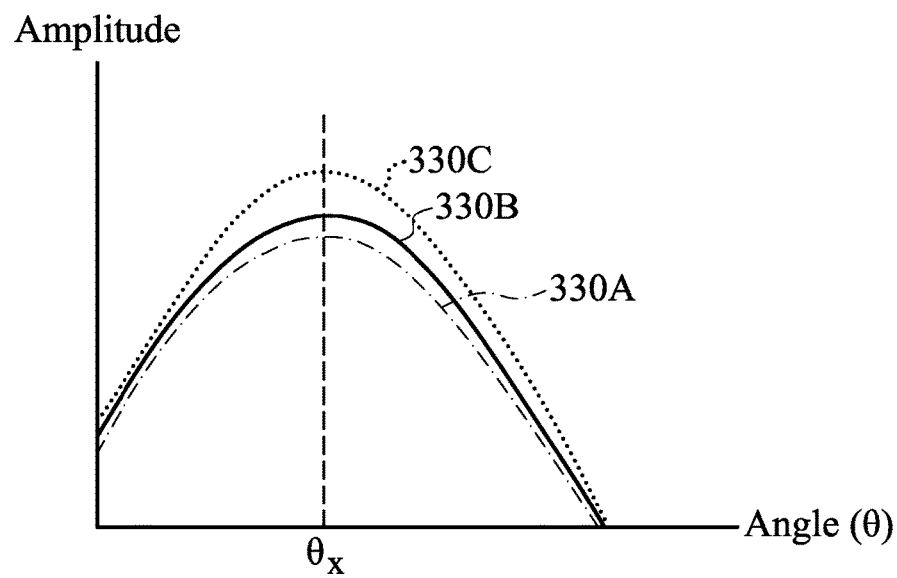
FIG. 5C is a magnified diagram showing the output signal of a detection device, in accordance with some embodiments.

The detection device 290 receives responses from the electrolyte solution 270 or 270' after each detection in the electrolyte solution 270 or 270'. As shown in FIG. 5B, output signals 330A, 330B and 330C are obtained after multiple detections, in accordance with some embodiments. The output signals 330A, 330B and 330C may be referred to as output curves or output data. In some embodiments, the output signals 330A, 330B and 330C are output currents and/or voltages. In some embodiments, the output signals 330A, 330B and 330C have a maximum difference or variation at the phase angle $\theta_x$. The phase angle $\theta_x$ may be in a range from about 0° to about 360°. FIG. 5C is a magnified diagram showing the portions of the output signals 330A, 330B and 330C around the phase angle $\theta_x$.

In accordance with some embodiments, applying the combination of AC and DC to the detection device 290 obtains obvious and reliable responses of the impurity 310 in the electrolyte solution 270, as shown in FIG. 5B or 5C. On the other hand, applying only AC or DC to the detection device 290 may not receive useful responses of the impurity 310 in the electrolyte solution 270. In some cases, if the combination of AC and DC is not within the aforementioned ranges of AC current, AC frequency, and DC voltage, the detection device 290 may not receive obvious responses of the impurity 310 in the electrolyte solution 270.

Figure 5D:
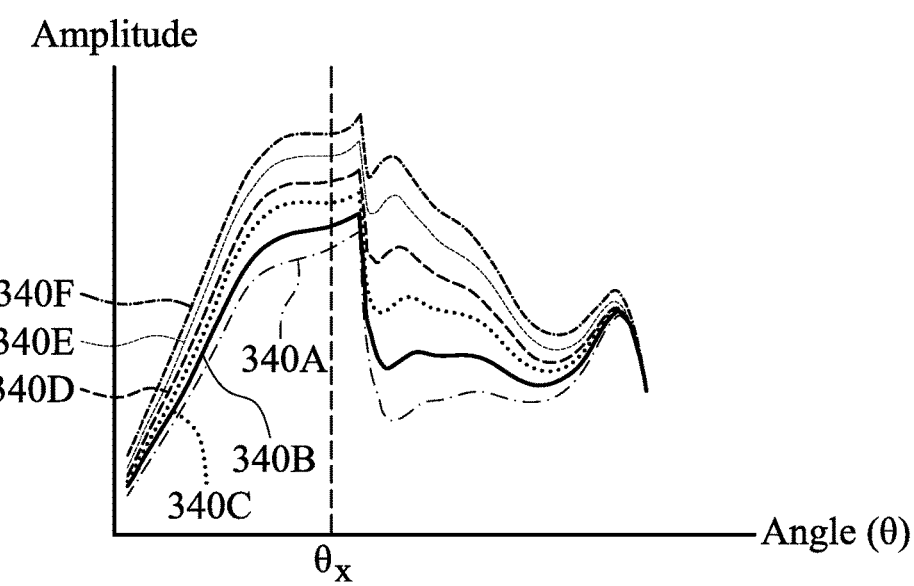
FIG. 5D is a diagram showing calibration data, in accordance with some embodiments.

As shown in FIG. 5D, calibration data including calibration curves 340A, 340B, 340C, 340D, 340E, and 340F is provided, in accordance with some embodiments. The calibration data can be used to analyze and identify the species and the concentration of the impurity 310. For example, the calibration curve 340A may be a base line, which means substantially no impurity 310. In some embodiments, the calibration curves 340B, 340C, 340D, 340E, and 340F represent different concentrations of the impurity 310. For example, the calibration curve 340B may represent a lower concentration of the impurity 310 than the calibration curves 340C, 340D, 340E, and 340F. In some other embodiments, the calibration curves 340B, 340C, 340D, 340E, and 340F represent different concentrations of various impurities.

In accordance with some embodiments, multiple experiments or tests are performed before electroplating processes so as to constructs calibration data. More specifically, in some embodiments, the probe 300 of the detection device 290 is immersed in the clean electrolyte solution 270 before performing electroplating processes. The combination of AC and DC (such as the input voltage 320 shown in FIG. 5A) is applied to the detection device 290. As a result, the detection device 290 receives an output signal or data from the clean electrolyte solution 270. The clean electrolyte solution 270 may be detected multiple times to obtain an average output signal. The (average) output signal constructs a base line of the calibration data (such as the calibration curve 340A).

In some embodiments, the probe 300 of the detection device 290 is immersed in various electrolyte solutions containing the impurity 310 (or different impurities). Each of the electrolyte solutions has a different concentration of the impurity 310. The combination of AC and DC (such as the input voltage 320 shown in FIG. 5A) is applied to the detection device 290. As a result, the detection device 290 receives multiple output signals from the electrolyte solutions containing the impurity 310. The electrolyte solutions containing the impurity 310 may be detected multiple times to obtain an average output signal of each electrolyte solution. The (average) output signal of each electrolyte solution constructs different calibration curves of the calibration data (such as the calibration curves 340B, 340C, 340D, 340E, and 340F).

Figure 5E:
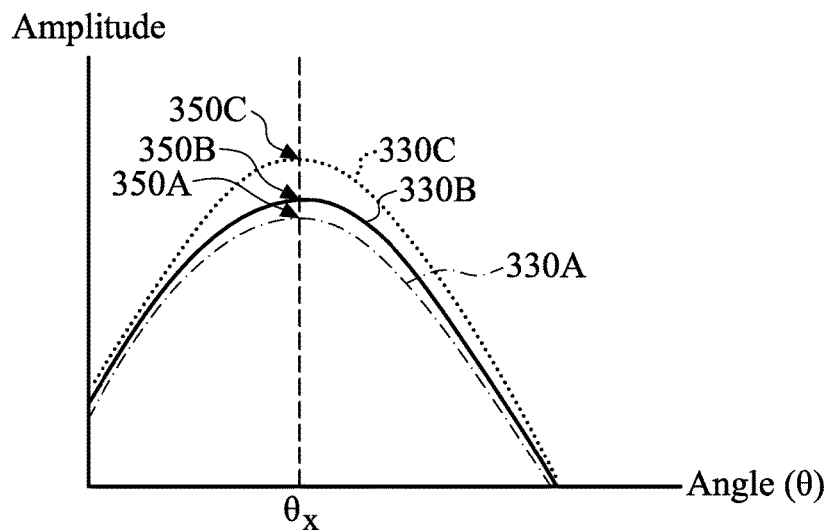
FIG. 5E is a magnified diagram showing the output signal of a detection device, in accordance with some embodiments.

In accordance with some embodiments, an output signal obtained during or between electroplating processes is compared with the calibration data. For example, in some embodiments, the resulted output signal 330A shown in FIG. 5B or 5C is compared with the calibration data shown in FIG. 5D. As a result, the output signal 330A at the phase angle $\theta_x$ substantially matches the calibration curve 340A at the phase angle $\theta_x$, as shown in FIG. 5E. It can be identified that the electrolyte solution 270 examined by the detection device 290 has a concentration 350A of the impurity 310. When the calibration curve 340A is a base line, it means that the electrolyte solution 270 is clean and substantially free of the impurity 310. Therefore, the electrolyte solution 270 does not need to be replaced yet.

In some embodiments, the resulted output signal 330B shown in FIG. 5B or 5C is compared with the calibration data shown in FIG. 5D. As a result, the output signal 330B at the phase angle $\theta_x$ substantially overlaps the calibration curve 340B at the phase angle $\theta_x$, as shown in FIG. 5E. It can be identified that the electrolyte solution 270 examined by the detection device 290 has a concentration 350B of the impurity 310. For example, the concentration 350B of the impurity 310 may be in a range from about 5% to about 10%.

In some embodiments, the calibration curve 340B represents the concentration of by-products in the electrolyte solution 270. If the concentration 350B is greater than or equal to a predetermined concentration of by-products, it may imply that the electrolyte solution 270 becomes not clean enough. Therefore, the electrolyte solution 270 will be replaced with a clean electrolyte solution so as to maintain high quality of electroplating processes.

In some embodiments, the resulted output signal 330C shown in FIG. 5B or 5C is compared with the calibration data shown in FIG. 5D. As a result, the output signal 330C at the phase angle $\theta_x$ substantially overlaps the calibration curve 340D at the phase angle $\theta_x$, as shown in FIG. 5E. It can be identified that the electrolyte solution 270 examined by the detection device 290 has a concentration 350C of the impurity 310.

In some embodiments, the calibration curve 340B and the calibration curve 340D represents the concentration of different by-products in the electrolyte solution 270. Since the output signal 330C at the phase angle $\theta_x$ substantially overlaps the calibration curve 340D at the phase angle $\theta_x$, it can be identified that the electrolyte solution 270 examined by the detection device 290 contains a specific by-product having the concentration 350C.

Many variations and/or modifications can be made to embodiments of the disclosure. For example, the aforementioned embodiments provide a detection method, which compares output curves with calibration curves, but embodiments of the disclosure are not limited. In some other embodiments, the calibration curves are calculated, quantified and transformed to a calibration table, which directly show values of concentration of various impurities. The output curves may also be calculated and then compared with the calibration table so as to analyze the species and the concentration of the impurity 310 in the electrolyte solution 270. It is able to identify if there is any contaminant and/or by-product in the electrolyte solution 270 and find out the concentration of the by-product.

When there is any contaminant in the electrolyte solution 270, the electrolyte solution 270 in the plating bath 210 and the reservoir 220 is removed. Another electrolyte solution 270', which is cleaner than the previous electrolyte solution 270, is added in the plating bath 210 and the reservoir 220. When the by-product(s) in the electrolyte solution 270 is too much or more than a predetermined concentration, the original electrolyte solution 270 in the plating bath 210 and the reservoir 220 is renewed and replaced by a clean electrolyte solution 270'. Therefore, the quality of electroplating processes is enhanced.

Figure 6:
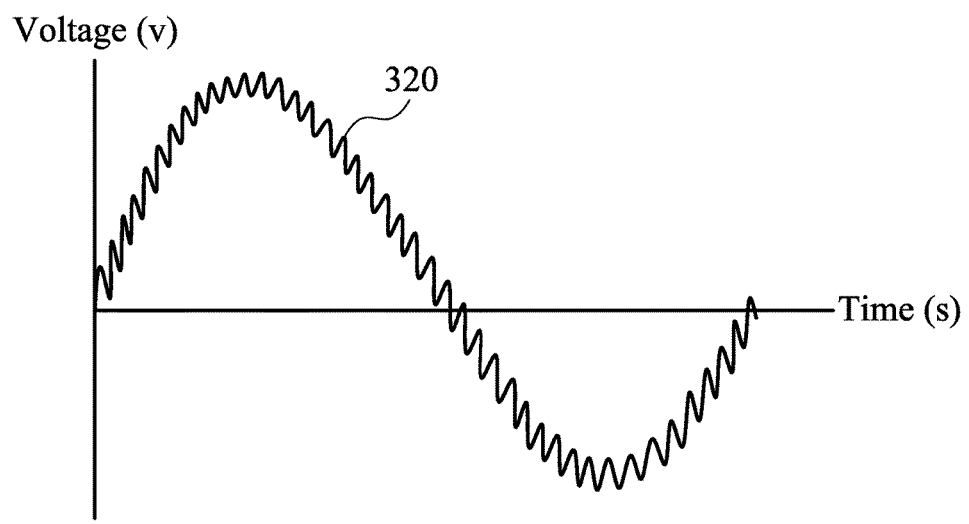
FIG. 6 is a diagram showing the input voltage of a detection device, in accordance with some embodiments.
Figure 7:
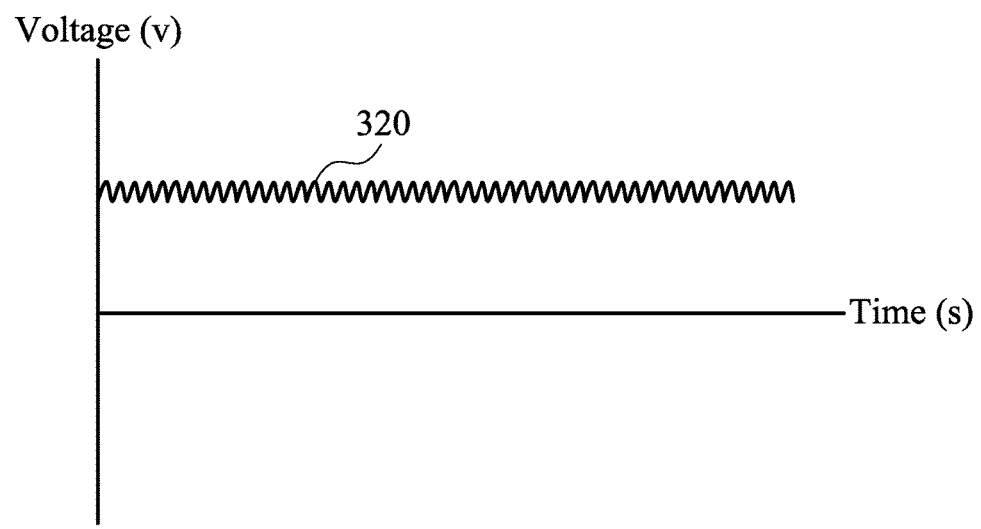
FIG. 7 is a diagram showing the input voltage of a detection device, in accordance with some embodiments.

Many variations and/or modifications can be made to embodiments of the disclosure. For example, the combination of AC and DC is not limited to the input voltage 320 shown in FIG. 5A. In some embodiments, the main waveform of the input voltage 320 is a sine wave, as shown in FIG. 6. The main waveform of the input voltage 320 may be a raised sine wave or an inverse sine wave. In some embodiments, the main waveform of the input voltage 320 is a flat and straight wave, as shown in FIG. 7. The main waveform of the input voltage 320 may be a positive wave or a negative wave. In some other embodiments, the main waveform of the input voltage 320 is a raised cosine wave, an inverse cosine wave, a square curve, another suitable curve, or a combination thereof.

In some embodiments, the detection methods for an electroplating process described in the disclosure are used to form an interconnection structure of a semiconductor device, as shown FIGS. 1A-1C. However, embodiments of the disclosure are not limited. In some other embodiments, the detection methods for an electroplating process described in the disclosure can be used to form any suitable conductive structures. Embodiments of the disclosure are not limited and can be applied to fabrication processes for any suitable technology generation. Various technology generations include a 28 nm node, a 20 nm node, a 16 nm node, a 10 nm node, a 7 nm node, a 5 nm node, or another suitable node.

Embodiments of the disclosure provide detection methods to inspect an electrolyte solution during or between electroplating processes for fabrication of semiconductor devices. A detection device, such as a device including one or more metal probes, is used to detect impurities in the electrolyte solution. The impurities include one or more contaminants, one or more by-products, or a combination thereof. Both alternating current and direct current are input to the detection device. As a result, the species and the concentration of the impurities can be identified according to feedback or responses from the electrolyte solution to the detection device. It can be ensured that the electrolyte solution maintains sufficiently clean during the electroplating processes. The electrolyte solution can be timely replaced with a cleaner electrolyte solution so as to improve the quality of the electroplating processes. Therefore, the circuit performance and reliability of semiconductor devices is enhanced even further.

In accordance with some embodiments, a detection method is provided. The detection method includes immersing a substrate into an electrolyte solution to perform an electroplating process. The electrolyte solution includes an additive agent. The detection method also includes immersing a detection device into the electrolyte solution. The detection method further includes applying a first alternating current (AC) or direct current (DC) to the detection device to detect the concentration of the additive agent. In addition, the detection method includes applying a combination of a second AC and a second DC to the detection device to inspect the electrolyte solution. An impurity is detected in the electrolyte solution. The detection method also includes replacing the electrolyte solution containing the impurity with another electrolyte solution.

In accordance with some embodiments, a detection method is provided. The detection method includes dipping a first probe into a first electrolyte solution in an electrochemical plating device. The detection method also includes applying an alternating current (AC) and a direct current (DC) together to the first probe to inspect the first electrolyte solution. An impurity is detected in the first electrolyte solution. The detection method further includes removing the first probe from the first electrolyte solution. In addition, the detection method includes replacing the first electrolyte solution containing the impurity with a second electrolyte solution. The. The detection method also includes dipping the first probe into the second electrolyte solution. The detection method further includes applying the AC and the DC together to the first probe to inspect the second electrolyte solution.

In accordance with some embodiments, a detection method is provided. The detection method includes immersing a substrate into a first plating solution to perform an electroplating process. The detection method also includes immersing a detection device into the first plating solution. The detection method further includes applying an alternating current (AC) and a direct current (DC) to the detection device simultaneously so that the detection device in the first plating solution receives a first output signal. In addition, the detection method includes comparing the first output signal with calibration data to identify an impurity in the first plating solution.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A detection method, comprising:
   immersing a substrate into an electrolyte solution to perform an electroplating process, wherein the electrolyte solution comprises an additive agent;
   immersing a detection device into the electrolyte solution;
   applying a first alternating current (AC) voltage or direct current (DC) voltage to the detection device to detect a concentration of the additive agent;
   applying a combination of a second AC voltage and a second DC voltage to the detection device to inspect the electrolyte solution, wherein an impurity is detected in the electrolyte solution;
   receiving an output signal using the detection device after the application of the combination of the second AC voltage and the second DC voltage to the detection device;
   matching an output curve of the output signal to calibration curves of calibration data at a phase angle to identify the impurity and/or a concentration of the impurity; and
   replacing the electrolyte solution containing the impurity with another electrolyte solution.

2. The detection method as claimed in claim 1, wherein the electrolyte solution is simultaneously in contact with the substrate and with the detection device during the application of the combination of the second AC voltage and the second DC voltage to the detection device.

3. The detection method as claimed in claim 1, wherein the combination of the second AC voltage and the second DC voltage is applied to the detection device before or after the application of the first AC voltage or DC voltage to the detection device.

4. The detection method as claimed in claim 1, wherein the additive agent comprises an accelerator, a suppressor, a leveler, or a combination thereof, and wherein the impurity in the electrolyte solution is different from the accelerator, the suppressor and the leveler.

5. The detection method as claimed in claim 1, wherein the additive agent decomposes into the impurity during the electroplating process.

6. The detection method as claimed in claim 1, wherein the impurity in the electrolyte solution comprises a cleaning agent for washing the substrate.

7. The detection method as claimed in claim 1, wherein a frequency of the second AC voltage is in a range from about 5 Hz to about 3E+6 Hz, and the second DC voltage is in a range from about −5 V to about 10 V.

8. The detection method as claimed in claim 1, wherein a frequency of the first AC voltage is in a range from about 10 Hz to about 4000 Hz, and the first DC voltage is in a range from about −10 V to about 10 V.

9. A detection method, comprising:
   dipping a first probe into a first electrolyte solution in an electrochemical plating device;
   applying an alternating current (AC) voltage and a direct current (DC) voltage together to the first probe to inspect the first electrolyte solution, wherein an impurity is detected in the first electrolyte solution;
   obtaining a first output curve from the first electrolyte solution using the first probe;
   matching the first output curve with calibration curves at a phase angle to identify the impurity in the first electrolyte solution;

removing the first probe from the first electrolyte solution;
replacing the first electrolyte solution containing the impurity with a second electrolyte solution; dipping the first probe into the second electrolyte solution; and
applying the AC voltage and the DC voltage together to the first probe to inspect the second electrolyte solution;
obtaining a second output curve from the second electrolyte solution using the first probe;
comparing the second output curve with calibration curves at a phase angle to identify the impurity in the second electrolyte solution.

10. The detection method as claimed in claim 9, further comprising:
dipping a second probe into the first electrolyte solution to detect a concentration of an additive agent in the first electrolyte solution, wherein the impurity is different from the additive agent; and
removing the second probe from the first electrolyte solution.

11. The detection method as claimed in claim 10, wherein an additional AC voltage or DC voltage is applied to the second probe to detect the concentration of the additive agent during the application of the AC voltage and the DC voltage together to the first probe.

12. The detection method as claimed in claim 10, wherein the first electrolyte solution is simultaneously in contact with the first probe and with the second probe.

13. The detection method as claimed in claim 10, wherein the first electrolyte solution is in a plating bath and a reservoir of the electrochemical plating device, and wherein the first probe is inserted into the plating bath and the second probe is inserted into the reservoir.

14. The detection method as claimed in claim 10, wherein the additive agent comprises an accelerator, a suppressor, a leveler, or a combination thereof.

15. The detection method as claimed in claim 9, wherein the impurity in the first electrolyte solution comprises an oil and/or a cleaning solution in the electrochemical plating device.

16. A detection method, comprising:
immersing a substrate into a first plating solution to perform an electroplating process;
immersing a detection device into the first plating solution;
applying an alternating current (AC) voltage and a direct current (DC) voltage to the detection device simultaneously so that the detection device in the first plating solution receives a first output signal; and
comparing the first output signal with calibration data to identify an impurity in the first plating solution, wherein the comparison of the first output signal with the calibration data comprises matching an output curve of the first output signal to calibration curves of the calibration data at a phase angle to determine a concentration of the impurity, and wherein the first plating solution comprises additive agents, and the impurity comprises a by-product formed from the additive agents during the electroplating process.

17. The detection method as claimed in claim 16, further comprising:
removing the detection device from the first plating solution; and
replacing the first plating solution containing the by-product with a second plating solution after a concentration of the by-product is greater than a predetermined concentration.

18. The detection method as claimed in claim 16, wherein the additive agents comprise an accelerator, a suppressor, a leveler, or a combination thereof.

19. The detection method as claimed in claim 16, further comprising:
monitoring concentrations of the additive agents in the first plating solution using the detection device before or after the application of the AC voltage and the DC voltage to the detection device; and
removing the detection device from the first plating solution after the concentrations of the additive agents are detected by the detection device and after the detection device receives the first output signal.

20. The detection method as claimed in claim 19, wherein a time for detecting the impurity in the first plating solution is different from a time for detecting the concentrations of the additive agents in the first plating solution.

* * * * *